(12) United States Patent
Bobrowski

(10) Patent No.: US 7,208,183 B2
(45) Date of Patent: Apr. 24, 2007

(54) METHODS AND PREPARATIONS OF THE LATEX FROM THE CROTON SPECIES

(76) Inventor: Paul J. Bobrowski, 5030 E. Libby St., Scottsdale, AZ (US) 85254

( * ) Notice: Subject to any disclaimer, the term of this patent is extended or adjusted under 35 U.S.C. 154(b) by 133 days.

(21) Appl. No.: 10/674,587

(22) Filed: Sep. 30, 2003

(65) Prior Publication Data

US 2004/0067269 A1 Apr. 8, 2004

Related U.S. Application Data

(60) Provisional application No. 60/416,751, filed on Oct. 5, 2002.

(51) Int. Cl.
*A61K 36/00* (2006.01)
(52) U.S. Cl. ............... 424/779; 424/775; 424/776
(58) Field of Classification Search ............... 424/779
See application file for complete search history.

(56) References Cited

U.S. PATENT DOCUMENTS

| | | | | |
|---|---|---|---|---|
| 4,061,643 A | * | 12/1977 | Cragoe et al. | 546/301 |
| 4,716,179 A | * | 12/1987 | Hecker et al. | 514/691 |
| 5,156,847 A | | 10/1992 | Lewis et al. | |
| 5,211,944 A | | 5/1993 | Tempesta | |
| 5,494,661 A | | 2/1996 | Tempesta | |
| 5,928,646 A | * | 7/1999 | Nkiliza | 424/773 |

FOREIGN PATENT DOCUMENTS

WO    WO 0047062    *  8/2000

OTHER PUBLICATIONS

Ubillas et al; "SP-303, an Antiviral Oligomeric Proanthocyanidin from the Latex of *Croton lechleri* (Sangre de Drago)," Gustav Fischer Verlag, Phytomedicine vol. 1/1994, pp. 77-106.*
Rinaldo Marini Bettolo & M. Luisa Scarpati, Alkaloids of *Croton draconoides*, Article, 1 page, 1979.
Georgia Persinos Perdue et al., South American Plants II: Taspine Isolation and Anti-Inflammatory Activity, J. of Pharmaceutical Sciences, V68 No. 1 Jan. 1979, p. 124 U.S.
Abraham J. Vaisberg et al., Taspine is the Cicatrizant Principle in Sangre de Grado Extracted from *Croton lechleri*, Plant Medica 55 (1989), pp. 140-143, U.S.
Luc Pieters et al., Isolation of a Dihydrobenzofuran Ligan from South American Dragon's Blood (*Croton* spp.) as an Inhibitor of Cell Proliferation, 1993, U.S.
J. David Phillipson, A Matter of Some Sensitivity, PhytoChemistry, vol. 38 No. 6 pp. 1319-1343, 1995 U.S.
Mark J.S. Miller et al., Inhibition of Neurogenic Inflammation by the Amazonian Herbal Medicine Sangre de Grado, J. Invest Dermatology 117:725-730, 2001, U.S.
S.E. Gabriel et al., A Novel Plant-Derived Inhibitor of cAMP-mediated fluid and Chloride Secretion, Am. J. Physiol. 267, G58-63, 1999, U.S.
Mark Holodniy, M.D. et al., A Double Blind Randomized, Placebo-Controlled Phase II Study to Assess the Safety and Efficacy . . . Am. J. Gastroenterology, vol. 94, No. 11, 1999, U.S.
Beate Illek et al., A novel extract from the bark latex of *Croton lechleri* inhibits cAMP-mediated chloride secretion . . . , Dec. 2000, U.S.
Mark J.S. Miller et al., Treatment of gastric ulcers and diarrhea with the Amazonian herbal medicine . . . , Am J Phisiol Gastrointes Liver Physiol 279: G192-200, 2000.
Manuel Sandoval, Sangre de grado *Croton palanostigma* induces apoptosis in human gastrointestinal cancer cells, J. Ethno-Pharmacology, 80, pp. 121-129, 2002, U.S.
Zheng-Ping Chen et al., Studies on the Anti-Tumour, Anti-Bacterial, and Wound-Healing Properties of Dragon's Blood, Planta Med. 60 (1994) 541-545.

* cited by examiner

*Primary Examiner*—Christopher Tate
*Assistant Examiner*—S. B. McCormick-Ewoldt
(74) *Attorney, Agent, or Firm*—Venable Campillo Logan & Meaney, P.C.

(57) ABSTRACT

The invention herein describes a procedure for organically extracting the lipophilic components from plants of the Family Euphorbaciae, specifically but not limited to the genus *Croton*. The extraction (CGO 110), is deplete of the normal proanthocyanidin content found in the parent material, yet retains its pharmacocological abilities and unlike the parent material, is selectively cytotoxic to cancer cells. The depletion of the proanthocyanidin components makes the product more amenable to preparations for the benefit of ameliorating both human and animal disease.

19 Claims, 4 Drawing Sheets

METHODS AND PREPARATIONS OF THE LATEX FROM THE CROTON SPECIES

This application claims benefit of U.S. Provisional Application Ser. No. 60/416,751 filed on Oct. 5, 2002.

BACKGROUND OF THE INVENTION

1. Field of the Invention

Sangre de grado or Sangre de drago, also known as "Dragon's Blood," is a viscous latex sap derived from the bark of various *Croton* species (*C. dracanoides, C. erythrochilus, C. gossypifilius, C. lechleri, C. palanostigma, C. sakutaris* and *C. urucurana*) indigenous to the South American rainforests. This latex has a deep red or burgundy color that is attributed to its substantial proanthocyanidin content, estimated to being approximately 90% of the solid constituents of the sap. Ethnomedically, the latex is topically applied for the treatment of pain and itching associated with insect bites and stings, as well as plant reactions. It is applied to the gums of patients after tooth extractions, is utilized as a vaginal wash in the case of excessive bleeding and in the treatment of herpes where it is applied topically. It is also applied to open wounds as an anti-infective and as a cicatrizant to accelerate the healing process. This latter effect may result from its constitutive taspine and crolechleric acid. It is taken internally for a variety of distressing gastrointestinal symptoms, including the treatment of diarrhea, ulcers, vomiting and gut inflammation, as well as throat infections, tuberculosis and rheumatism. Oral intake is also associated with the ethnomedical application for cancer.

These traditional applications within South America cultures are less likely to be used in the Western world because of several constraints. Primarily, Sangre de grado's intense color, as suggested by the reference to blood in its name, limits its ability to be used topically. In addition, Sangre de grado discolors and stains clothing in a similar manner as red wine, another proanthocyanidin rich extract. A means of reducing the proanthocyanidin content (and hence color) of the latex whilst retaining its useful biological properties would represent a significant improvement over the traditional botanical and allow for more widespread application.

The proanthocyanidins have been implicated as the mediators of Sangre de grado's antidiarrheal properties through the prevention of cAMP mediated epithelial secretion. However, recent evidence suggests that Sangre de grado attenuates these epithelial secretory mechanisms by preventing the activation of sensory afferent nerves that promote diarrhea, local inflammation, edema, as well process signals to the brain for pain, nausea and itching. Capsaicin, the active component of chili peppers, stimulates these sensory afferent nerves and Sangre de grado has been shown to impair capsaicin-induced epithelial secretion of electrolytes.

SUMMARY OF THE INVENTION

Aspects of the invention are summarized below to aid in the understanding of embodiment(s) of the invention and the application. Yet, the invention is fully defined by the claims of the application.

The latex or sap derived from the bark of the *Croton* species of the South American rainforests is associated with various ethnomedical applications including the treatment of cancer, diarrhea, gastrointestinal distress, pain and itching. While effective for these indications the traditional ethnomedicine has undesirable effects that limit its use.

The present invention generally comprises an extract composition derived from the latex or sap of the *Croton* species that retains desirable medicinal benefits despite reduced proanthocyanidin content. The extract disclosed herein retains the ability to inhibit emesis and activation of sensory afferent nerves. The extract furthermore discriminately promotes cancer cell death, unlike the parent material, at concentrations that fail to promote cell death in normal cells. The extract composition retains its desirable properties but has a reduced cytotoxicity signifying an improvement over the parent botanical.

The extract composition is further incorporated into a biologically active dosage unit forming a beneficial wound-healing composition.

DESCRIPTION OF AN EMBODIMENT

Extraction Procedure

Figure 1:
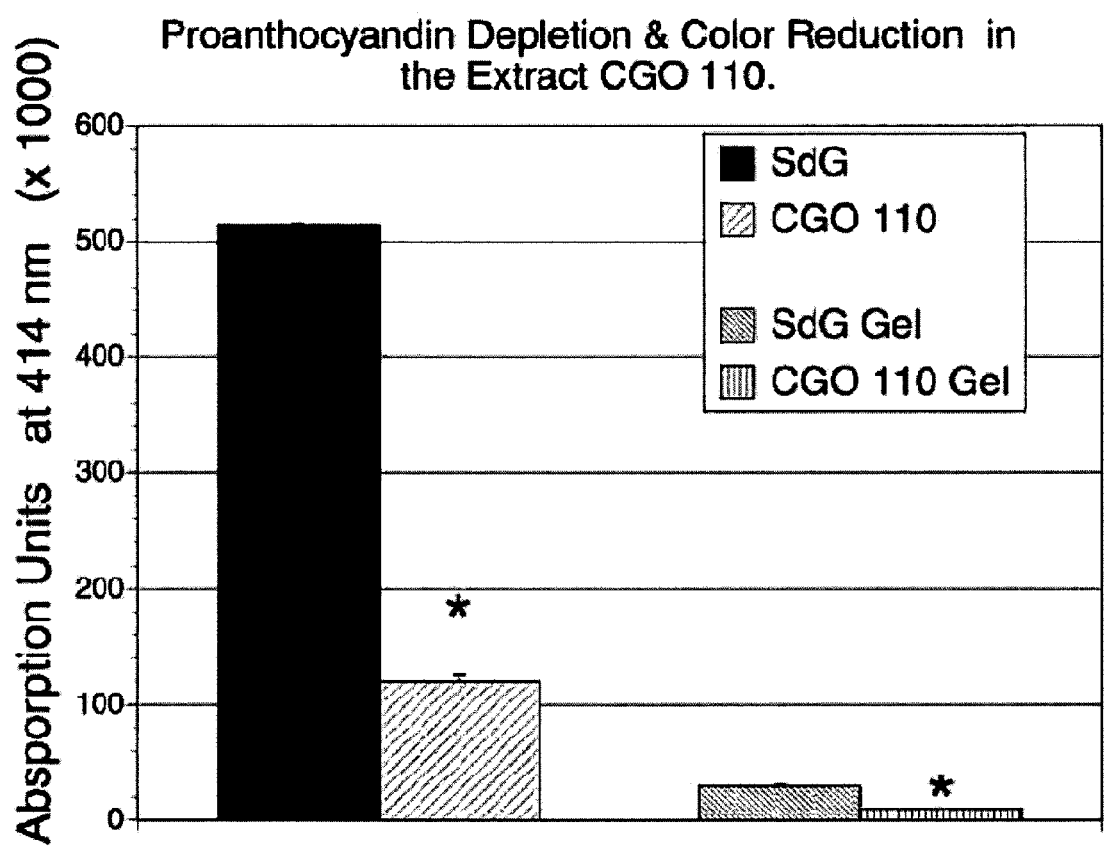
FIG. 1. The extraction process significantly ("*") reduces the proanthocyanidin content of the parent latex (SdG) from the species *Croton lechleri* from the family Euphorbaceae. When combined in a base vehicle, such as *Aloe barbadensis* shown here, the extract (CGO 110) produced a mixture absent of the intense color seen in similar preparations with the parent latex. This change, which is readily quantifiable by spectrophotometer, negates the discoloring (i.e. staining) properties commonly associated with proanthocyanidins and the parent latex and allows for practical dermatological preparations.

According to one aspect of this invention, a process that retains and concentrates the lipophilic components while reducing the hydrophilic proanthocyanidin content of the plant material resolves a family Euphorbaciae extraction. This extraction process significantly reduces the extracted composition of the hydrophilic proanthocyanidins, and hence its intense burgundy color, making it more amenable to topical health care preparations. Furthermore, a product of this lipidic extraction, is embodied in CGO 110 from the species *Croton lechleri* from the family Euphorbaceae, is selectively cytotoxic to cancerous cells, unlike the parent material, representing an improvement in safety and suggesting applications in the treatment of cancerous cells. Preferred methods to accomplish the aforementioned family Euphorbaceae extraction are described by the procedures below but it is contemplated that a skilled practitioner could device obvious variations of the procedures given the disclosure herein and the desired results.

Extraction Process 1.

Latex, or sap from *Croton* species is mixed with an organic solvent. The preferred organic solvent is ethyl acetate although other organic solvents can be used as would be obvious to the ordinarily skilled practitioner in light of the disclosure herein. In other embodiments, the preferred organic solvent is isopropanol, a chloroform/Methanol mixture, or an equivalent thereof. The organic solvent is added to the latex in a 1:1 proportion. In the preferred extraction process the solvent latex combination is agitated.

The preferred agitation method is stirring although other agitation methods are also contemplated to be effective. Following agitation, the mixture is settled, or allowed to settle into distinct phases including at least an organic layer and an aqueous layer. The organic phase or layer is comprised largely of solute lipophilic materials, representing the active constituent, and a significantly reduced quantity of proanthocyanidin components relative to the pre-agitation step. The organic layer is separated from the aqueous layer for further processing pursuant to the preferred extraction process.

Moreover, it is common to find a gel-like substance in the organic layer at the interface of the aqueous and organic layers. This gel substance is characterized as having a dark brown and purple color and comprises hydrophilic constituents trapped with water. In the preferred process the gel substance is processed further to separate any active lipophilic constituents from the hydrophilic constituents. The preferred manner of processing the gel substance is the addition of a drying agent to the organic layer or the gel substance. The preferred drying agent is magnesium sulfate in a concentration of 0.5–5 g/L of contaminant gel. It is contemplated that other equivalent drying agents at relative effective concentrations would also be effective and would be obvious to the ordinarily skilled practitioner in light of the disclosure herein and with undue experimentation.

The addition of the drying agent results in a precipitant, which traps water and hydrophilic constituents or water-based colored chemical contaminants. The precipitant can be readily separated from the hydrophilic constituents by filtration or other techniques known to separate precipitants. Actual laboratory procedures achieved acceptable results using a Whatman #4 filter paper or an equivalent.

The steps of organic extraction, mixing with a drying agent and filtration may be repeated up to three times to accomplish a thorough extraction of the active lipophilic constituents. At this point in the process, the lipophilic materials are solutes contained within the organic solvent, which are concentrated by evaporation of the solvent by one of several procedures, such as vacuum drying, freeze drying or heating. Actual heating up to 60 degrees Celsius produced acceptable drying results.

The organic layer composition thus processed is rich in lipophilic materials but largely clear of hydrophilic contaminants. Following the extraction process, the color of the organic layer can be characterized as a rose. Moreover, the reduced proanthocyanidin content is quantifiable spectrophotometrically. Relative absorbance of the extraction in the visible spectrum was compared to the absorbency peak of the parent latex (414 nm) in the visible range.

A product (CGO 110) of the extraction process disclosed herein is from the species *Croton lechieri* from the family Euphorbaceae. At a concentration of 1 mg of extracted latex to 1 mL of water the disclosed process yielding the extraction (CGO 110) results in a 4.3 fold reduction in absorbance at 414 nm, as indicated in FIG. 1. This assessment was repeated 9 times with similar results achieved (significance difference P<0.0001, as denoted by the "*"). Similarly when sangre de grado or the extraction (CGO 110) at a concentrations of 200 µg per mL of *aloe vera* gel were applied to *aloe vera* gel to mimic their administration as topical products, there was also a significantly lower color response with the extracted sangre de grado, CGO 110 vs. the parent botanical (*P<0.0001). See FIG. 1. Estimates from the absorbency measurements indicate that the proanthocyanidin content was reduced by at least 90% relative to the nonextracted parent latex.

Extraction Process 2.

The latex from the *Croton* species is dried to its residual solid matter by methods such as heating, air-drying, vacuum or freeze-drying. The dried latex is rich in proanthocyanidin compounds and therefore characterized by a dark burgundy color. To the dried latex matter the organic solvent, ethyl acetate or an equivalent, is added. The dried latex and organic solvent mixture is agitated and the organic solvent is removed for further processing according to the procedure described in Example 1. This process may be repeated up to three times to accomplish a thorough extraction all lipophilic materials in the organic layer and solvent. If any water bearing contaminants are present, the addition of drying agent followed by filtration as noted above, will remove these contaminants. Removing the ethyl acetate through various methods including heating, air-drying, vacuum or freeze-drying then isolates the solutes contained within this organic extract.

The extraction thus processed according to the disclosed processes is characterized by a significant reduction of proanthocyanidin compounds. The reduction of the proanthocyanidin compounds leaves the extraction significantly diminished in color producing compounds and yet amenable to health care applications.

Reduced Proanthocyanidin Content and Color Reactions

FIG. 1 illustrates the extent of proanthocyanidin depletion accomplished by the extraction processes described herein. Relative absorbency of family Euphorbaciae latex Sangre de Grado (SdG) is compared against a similar quantity of the latex that has been processed according to one of the procedures disclosed herein (CGO 110). As shown in FIG.

1, the extraction processes significantly diminishes the proanthocyanidin compounds or content compared to the parent latex material and confirmed by a significant (500%) reduction in absorbency in the 390 to 430 nm range. Since this wavelength range is within the human visible range, the extraction representing a significant reduction in visible color of this organic extract compared to the parent material.

The presence of the proanthocyanidins in the parent latex provides a rich burgundy color to the ethnomedicine, however it also results in the generation of an intense "chocolate" color when combined with various base vehicles, including *Aloe barbadensis* (*aloe vera*) gel—and can thus act to stain various materials and textiles. In contrast, the mixture of the organic extract (CGO 110) with a similar base vehicle significantly reduces this color reaction, which can be readily quantified spectrophotometrically. FIG. 1 illustrates this result and compares, a similar quantity of *aloe barbadensis* gel, which has insignificant absorbency in the 390 nm to 430 nm range, mixed with a quantity of the parent latex (SdG Gel), and mixed with a similar quantity of parent latex extracted by a process disclosed herein (CGO 110 Gel).

Sangre de Grado has potential benefits as a topical applicant for various inflamed, itchy and irritated dermatological conditions. However, its inherent color due to a high proanthocyanidin content and thus the generation of an intense coloring when combined with base vehicles hinders its use for these applications. As the proanthocyanidin content and thus coloring are significantly reduced by the disclosed processes, alone or in combination with other topical crèmes, gels or base vehicles, the extraction (CGO 110) signifies a marked improvement in the natural product and its uses.

Effects of the Organic Extract on Sensory Afferents

A prototypical activator of sensory afferent nerves, the nerves that mediate the sensations of pain, itch, cough and nausea is capsaicin, the pungent chemical found in chili peppers. Activation of these nerves by an activator such as capsaicin leads to a multitude of responses including vasodilation (mediated by the release of neurotransmitters from these activated nerves that cause blood vessels to relax), inflammatory cell recruitment, edema, and the sensations of pain and itching. The Extraction (CGO 110) was tested to determine its ability to suppress sensory afferent nerve activation by testing its ability to inhibit capsaicin-induced increases in gastric blood flow.

Figure 2:
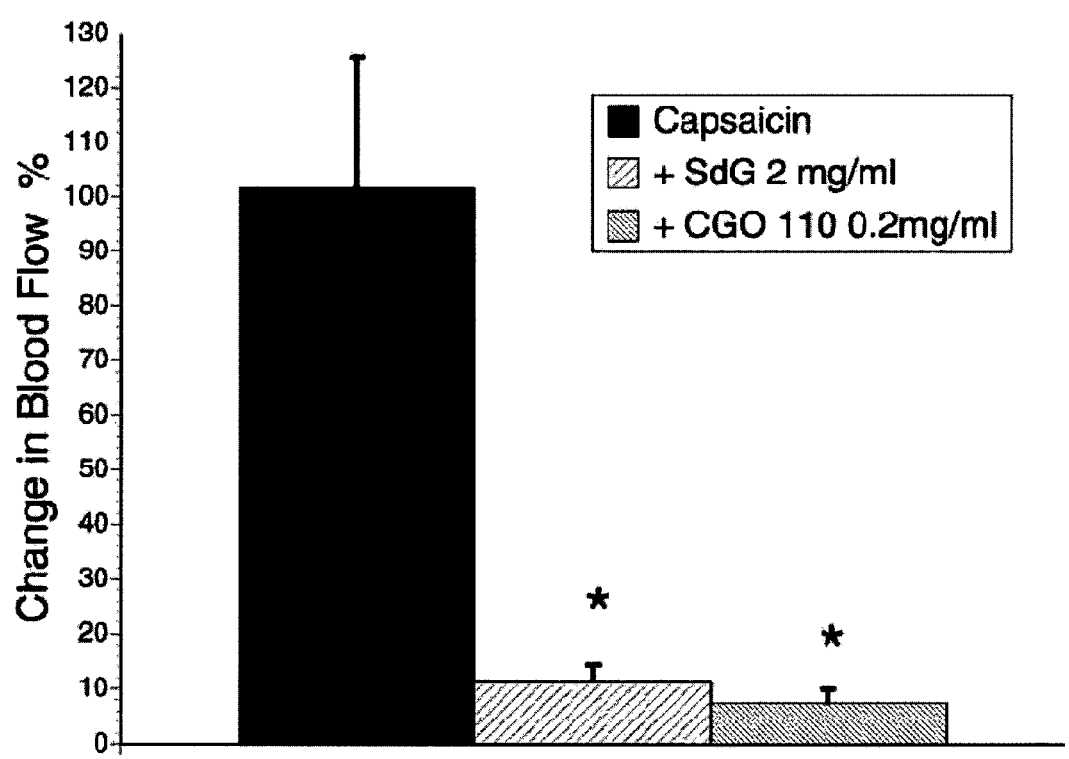
FIG. 2. The prototypical activator of sensory afferent nerves, capsaicin, was topically applied to the mucosal surface of the stomach in anesthetized rats and mucosal blood flow measured by a Laser Doppler Flow meter. The marked increase in mucosal blood flow induced by 300 μM capsaicin was prevented by either the parent material, SdG, or its organic extract, CGO 110 deplete of proanthocyanidins at doses of 2 and 0.2 mg/ml, respectively, indicating that the organic extract retains the ability to effectively prevent the activation of sensory afferent nerves.

The experiment involved the topical application of capsaicin to the mucosal surface of the stomach in anesthetized rats and mucosal blood flow measured by a laser Doppler flow meter. As indicated in FIG. 2, the marked increase in mucosal blood flow induced by 300 µM capsaicin was prevented by either the parent material, SdG, or its organic extract, CGO 110 deplete of proanthocyanidins at doses of 2 and 0.2 mg/ml, respectively. Thus, the organic extract described in this application retains the ability to effectively prevent the activation of sensory afferent nerves.

Effects on Morphine-Induced Emesis and Itch

Figure 3:
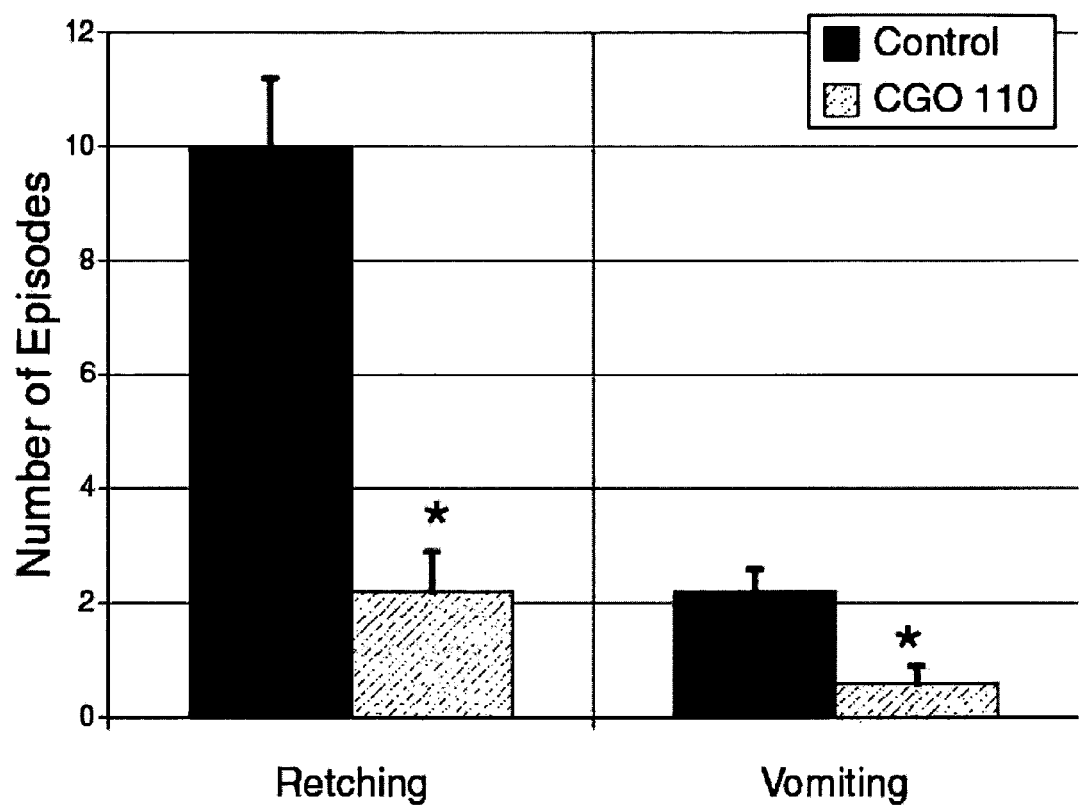
FIG. 3. Using a well-established ferret model of postoperative complications of nausea, emesis and itch induced by morphine, the organic extract CGO 110 was administered intraperitoneally (3 mg/kg) to ferrets 15 minutes prior to the subcutaneous injection of 0.05 mg/kg of morphine-6-glucuronide (M6G). Administration of M6G caused a significant number of vomiting (2.2±0.4) and retching (10±1.2) incidences in the control group while in those animals pretreated with CGO 110, the number of these episodes was virtually abolished (vomiting 0.6±0.3; retching 2.2±0.7, P<0.05). It is clear that this organic extraction procedure contains active components and is effective in the treatment of emesis and itch.

Sangre de Grado has also been used ethnomedically for the treatment of a variety of intestinal complications including diarrhea, ulcerations, cancer and emesis. Using a well-established ferret model of post-operative complications of nausea, emesis and itch induced by morphine, the extraction (CGO 110) was administered intraperitoneally (3 mg/kg) to ferrets 15 minutes prior to the administration of morphine-6-glucuronide (M6G), known to promote itching, retching and vomiting. The animals were monitored for sixty minutes. As shown in FIG. 3, the subcutaneous injection of 0.05 mg/kg M6G caused a significant number of vomiting (2.2±0.4) and retching (10±1.2) incidences in the control group. In those animals treated with extraction (CGO 110), the number of these episodes was virtually abolished (vomiting 0.6±0.3; retching 2.2±0.7, P<0.05). Itch as indicated by licking responses was reduced from a control value of 16.9±2.3 episodes to 2.2±0.7 in CGO 110 treated animals (P0.05). Given the utility of this model to predict treatments for itch, nausea and vomiting, the extraction (CGO 110) contains active components and is effective in the treatment of emesis and itch.

Cytotoxicity: Cancer Cell Selectivity

While Sangre de grado has traditional uses in the treatment of cancer, its utility is limited because it is equally toxic to both normal and cancerous cells. A process that could retain the ability of Sangre de grado to kill cancer cells but prevented these toxic effects on normal cells would represent a significant improvement over the traditional medicine and a benefit to the treatment of disease in both humans and animals.

To test the selective cytotoxic ability of extraction (CGO 110) in vitro, cancerous cells from the gastrointestinal tract (AGS: stomach) and both normal macrophages and normal intestinal epithelial cells (IEC-18) were utilized. Cancerous GI cells were chosen based on Sangre de grado's traditional application for gastrointestinal complications. Cell death was determined by the MTT assay [3-(4,5-dimethylthiazol-2yl)-2,5-diphenyltetrazolium bromide], which assesses cell number by virtue of its oxidative or respiratory activity and the generation of a dye detectable at a wavelength of 550 nm.

Figure 4:
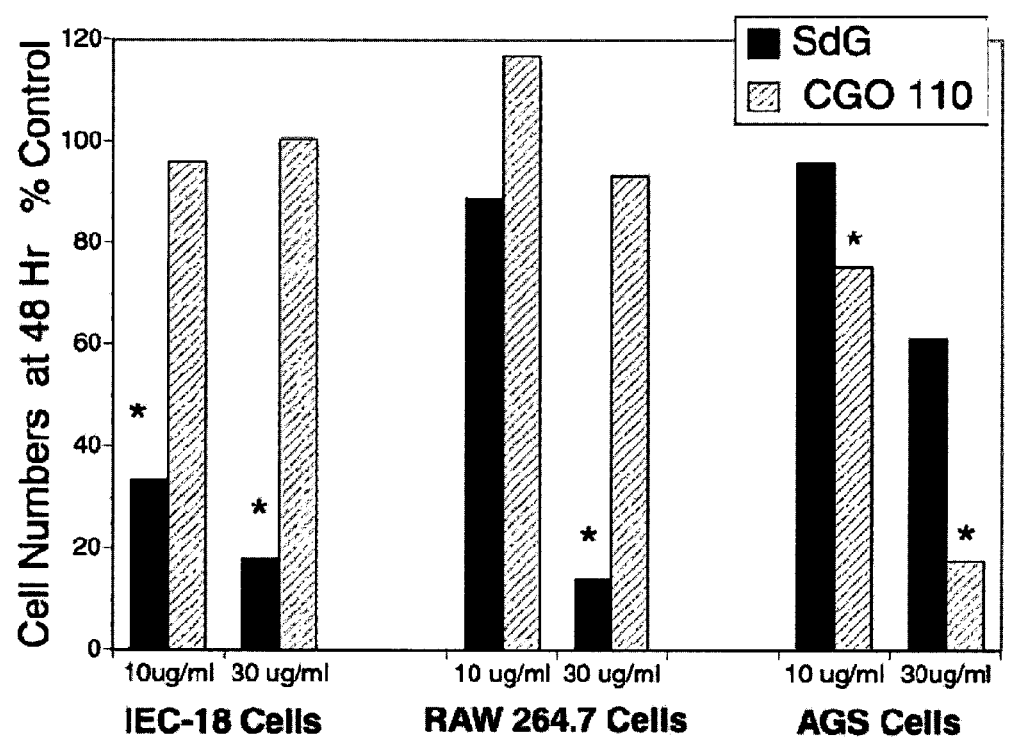
FIG. 4. The selective cytotoxic ability of CGO 110 was tested in vitro in cancerous cells from the gastrointestinal tract (AGS: stomach) and also in both normal macrophages and normal intestinal epithelial cells (IEC-18). In normal cells, Sangre de grado caused significant cell death in both macrophages and IEC-18 cells while the same concentrations of the organic extract CGO 110 did not. In stomach cancer cells (AGS), both CGO 110 and Sangre de grado were cytotoxic and the extract was more potent than the parent botanical. Treatment of stomach cancer cells (AGS) with both CGO 110 and Sangre de grado caused cytotoxicity (cell death), and the lipidic extract, CGO 110, was more potent than the parent botanical [the "*" denotes a significant difference between the Sangre de grado and organic extract CGO 110 formulations (P<0.05)]. Collectively, these results indicate that CGO 110 is selectively cytotoxic to cancerous cells compared to the parent botanical, thereby representing a marked improvement in safety.

As shown in FIG. 4, in normal cells, Sangre de grado caused significant cell death in both macrophages and IEC-18 cells while the same concentrations of the organic extract CGO 110 did not. From this we can determine that the lipidic extract CGO 110 has improved safety over the parent botanical. Treatment of stomach cancer cells (AGS) with both CGO 110 and Sangre de grado caused cytotoxicity (cell death), and the lipidic extract, CGO 110, was more potent than the parent botanical [the "*" in FIG. 4 denotes a significant difference between the Sangre de grado and organic extract CGO 110 formulations (P<0.05)]. Collectively, these results indicate that CGO 110 is selectively cytotoxic to cancerous cells compared to the parent botanical, thereby representing a marked improvement in safety.

Although the invention has been described in detail with reference to one or more particular preferred embodiments, persons possessing ordinary skill in the art to which this invention pertains will appreciate that various modifications and enhancements may be made without departing from the spirit and scope of the claims that follow.

What is claimed is:

1. A method of extracting lipophilic components from *Croton lechieri* comprising;
   combining plant material from *Croton lechieri* with an organic solvent;
   agitating the combination;
   settling the combination into distinct phases to resolve a layer substantially comprised of hydrophilic constituents and an organic layer substantially comprised of the lipophilic constituents;
   separating the organic layer from the layer substantially comprised of hydrophilic constituents; and
   evaporating the organic solvent from the organic layer to resolve the lipophilic constituents.

2. The method of claim 1 wherein,
   the plant material is latex.

3. The method of claim 1 wherein the organic solvent is selected from the group consisting of ethyl acetate, isopropanol and chloroform/Methanol mixture.

4. The method of claim 1 further comprising, adding a drying agent to the settled organic layer prior to the step of evaporating the organic layer to further precipitate any remaining hydrophilic constituents; and filtering the organic layer to resolve the lipophilic constituents.

5. The method in claim 4 wherein the drying agent selected from the group consisting of magnesium sulfate and sodium sulfate.

6. The method in claim 5 wherein the drying agent is magnesium sulfate and the amount added per liter of organic layer is between about five hundred milligrams (500 mg) to five grams (5 g) per liter.

7. The method in claim 4 wherein, after the step of filtering the organic layer, the organic layer at a concentration of one milligram per milliliter (1 mg/mL) of 50% (v/v) ethanol/water has an absorbance of about 0.120 Abs Units in the wavelength range between about 390 nm and about 430 nm, relative to an absorbency of about 515 Abs Units within the same wavelength range.

8. The method of claim 4 wherein the hydrophilic constituents having proanthocyanidin components are reduced by at least about 90% relative to the parent latex.

9. The method of claim 1 wherein the step of evaporating the precipitate to resolve the hydrophilic constituents is selected from the group of evaporating methods consisting of evaporation, spray drying, freeze drying, and vacuum drying.

10. A method for making an extract from *Croton lechieri;* combining plant material from *Croton lechieri* with an organic solvent;

agitating the combination;

settling the combination into distinct phases to resolve a layer predominantly comprised of hydrophilic constituents and an organic layer substantially comprised of the lipophilic constituents;

separating the organic layer from the layer substantially comprised of hydrophilic constituents; and evaporating the organic solvent from the organic layer to resolve the lipophilic constituents.

11. The method of claim 10 wherein, the organic solvent is selected from the group consisting of ethyl acetate, isopropanol and chloroform/Methanol mixture.

12. The method of claim 10 further comprising, adding a drying agent to the settled organic layer prior to the step of evaporating the organic layer to further precipitate any remaining hydrophilic constituents; and filtering the organic layer to retain the lipophilic constituents.

13. The method in claim 12 wherein the drying agent selected from the group consisting of magnesium sulfate and sodium sulfate.

14. The method in claim 13 wherein, the drying agent is magnesium sulfate and the amount added per liter of organic layer is between about five hundred milligrams (500 mg) to five grams (5 g) per liter.

15. The method in claim 12 wherein, after the step of filtering the organic layer, the organic layer at a concentration of one milligram per milliliter (1 mg/mL) of 50% (v/v) ethanol/water has an absorbance of about 0.120 Abs Units in the wavelength range between about 390 nm and about 430 nm, relative to an absorbency of about 515 Abs Units within said wavelength range.

16. The method of claim 12 wherein, the hydrophilic constituents comprising proanthocyanidin components are reduced by at least about 90% relative to the parent latex.

17. The method of claim 10 wherein, the step of evaporating the precipitate to resolve the hydrophilic constituents is selected from the group of evaporating methods consisting of evaporation, spray drying, freeze drying, and vacuum drying.

18. An extract from *Croton lechleri* made by the process of claim 12 wherein,

UV absorbency of the extract between a range of 390 nm and 430 nm is reduced by at least one-half relative to the absorbency for unextracted plant material within said range.

19. An extract as in claim 18 wherein, the UV absorbency of the extract between a range of 390 nm and 430 nm is about 0.010 Abs Units relative to about 0.030 Abs Units for unextracted plant material within said range.

* * * * *